United States Patent [19]
Nerli

[11] Patent Number: 5,571,412
[45] Date of Patent: Nov. 5, 1996

[54] DENTAL FILTER ASSEMBLY

[76] Inventor: Robert A. Nerli, 1370 Hayne Rd., Hillsborough, Calif. 94010

[21] Appl. No.: 331,124

[22] Filed: Oct. 28, 1994

[51] Int. Cl.$^6$ .................................................. B01D 27/00
[52] U.S. Cl. .................... 210/232; 210/167; 210/416; 210/435; 210/441; 210/444; 210/DIG. 17; 433/97
[58] Field of Search ...................................... 210/167, 232, 210/416.1, 435, 440, 437, 441, 442, 443, 444, DIG. 17; 433/97

[56] References Cited

U.S. PATENT DOCUMENTS

5,336,406  8/1994  Stanford et al. .................... 210/440
5,407,565  4/1995  Austin, Jr. et al. .................... 210/232

*Primary Examiner*—David A. Reifsnyder
*Attorney, Agent, or Firm*—Thomas M. Freiburger

[57] ABSTRACT

A filter canister assembly for receiving waste from a dental cuspidor includes a canister of generally conventional configuration, with an open upper end, fitted with a canister closure which engages with the upper end of the canister and which is secured to a disposable filter configured to fit within the canister. Embodiments are described wherein the canister closure is disposable and is permanently attached to the disposable filter; wherein the canister closure is snapped together with the filter; and wherein the filter itself has an annular ledge which seats with different sizes of canister, with the closure snapped into the upper end of the filter.

21 Claims, 6 Drawing Sheets

DENTAL FILTER ASSEMBLY

BACKGROUND OF THE INVENTION

The invention relates to dental equipment, and more specifically the invention is concerned with a changeable filter for a dental cuspidor.

Cuspidors for dental operatories are typically fitted with a filter assembly connected to receive the effluent waste (which includes blood and saliva from the dentist's patients) from the cuspidor. The filter typically has a plastic perforated filter screen, designed to remove most solids of significant size, along with blood and other materials associated with the solids. These solids include large particles of amalgam (containing mercury), the filter preventing them from entering the sewage system. The filter element, generally a basket-shaped element, is usually removed and changed daily. Although the filter element has conventionally been disposable and need not be cleaned, the task of changing the filter has been one of the most undesirable, distasteful jobs in the dental office, with a great possibility of cross infection, or infecting of the dental office staff.

A conventional filter canister has a canister body, and a lid or cover under which the filter basket is contained. The material from the cuspidor enters the filter canister from below, through one or several inlet tubes, passes through the filter and is discharged through an exit tube at the bottom of the canister, generally drawn by a vacuum, A conventional dental cuspidor filter canister is formed of a relatively tough but flexible plastic material which is integrally molded to include at least two tube connecting nipples at its bottom side, at least one for entry of liquid and solid material from the cuspidor, and at least one for the filtrate outlet. The canister has a generally cylindrical chamber which receives a basket shaped disposable filter to be dropped in from above. The inlet opening, or, as typically provided, the two inlet openings, have cylindrical collar extensions extending upwardly and vertically disposed inside the chamber, and the filter basket has similarly positioned cylindrical collars which slide down over and fit fairly closely on the inlet collars of the canister. Thus, with the filter basket in place, liquids entering the inlet or inlets will flow up through the filter basket collars and pour out into the canister plenum above the filter mesh, which is at the bottom of the filter basket.

When fully installed, the filter basket sits at a slightly elevated position above the bottom of the canister, such that a small space, e.g. about ¼ inch, is defined below the filter mesh and above the interior bottom of the canister. This space collects filtrate for exiting through the outlet in the bottom of the canister.

A vertical stem or post typically is formed integrally with the disposable filter basket, positioned in the center of the basket and being the uppermost extension of the filter basket. This stem enables gripping between the thumb and finger of the attendant, for removal and changing of the filter basket. Normally the stem is covered with cuspidor effluent.

At the top of the canister, a cover or lid of similar plastic to that of the canister is provided, often having some form of locking engagement device for securing to the canister, which may require placing the lid on the canister at a certain orientation followed by rotation to lock the lid in place. An O-ring may be included on the lid for sealing against a rim surface on the canister.

It is among the objects of the present invention to make easier and more efficient, and particularly to make less distasteful and safer, relative to cross-contamination and infection of dental staff, the task of changing the filter in a dental cuspidor filter assembly. A further object is to provide a filter structure which allows material (waste) to be disposed of into a waste disposal container, in a contained environment.

SUMMARY OF THE INVENTION

In accordance with the present invention, a filter canister for a dental cuspidor is formed with a lid or cover secured directly to a filter basket of the assembly, the lid and filter basket component being disposable. In a preferred embodiment the lid/filter basket fits onto an existing conventional filter canister, with the installation being similar, from the point of view of the user, to simply placing a conventional lid on the canister.

Thus, in one preferred embodiment a combination canister lid and filter for a dental cuspidor filter assembly includes a container of conventional configuration, generally defining a closed volume and having an upper open end, with an outlet in the container communicating with the closed volume and comprising an outlet tube or nipple for connection to a source of suction to be applied to the filter canister. At least one inlet tube communicates with the interior of the closed volume of the canister, for delivering waste material from the cuspidor to be filtered. A disposable canister closure or lid has means for engagement directly or indirectly with the container and for providing a seal with the container when engaged with the upper open end. Affixed to the canister closure is a preferably disposable filter, positioned when installed in the container so as to receive suction from the outlet tube against an outlet side of the filter and to receive waste material from the inlet tube at an inlet side of the filter. Either the lid or an outer rim of the filter basket engages against the top edge of the canister. Thus, the filter of the dental filter canister can be quickly changed by removal and disposal of the canister closure and attached filter and replacement with a similar new disposable canister closure/filter combination.

Another element of the invention may be included in the event the dental practitioner is required to dispose of materials filtered-out by the filter basket in a secure container. A snap-on or friction fit plastic bottom piece is provided to secure over the bottom of the filter basket, thus closing the entire filter basket.

It is therefore the main object of this invention to make more efficient, fast and sanitary the task of changing the filter in a dental cuspidor filter assembly, specifically by making the lid and filter basket a single component which is preferably disposable and which eliminates contaminating contact. Another object is to allow containment of filtered-out effluent material for removal to a safe disposal container. These and other objects, advantages and features of the invention will be apparent from the following description of a preferred embodiment, considered along with the accompanying drawings.

DESCRIPTION OF PREFERRED EMBODIMENTS

Figure 1:
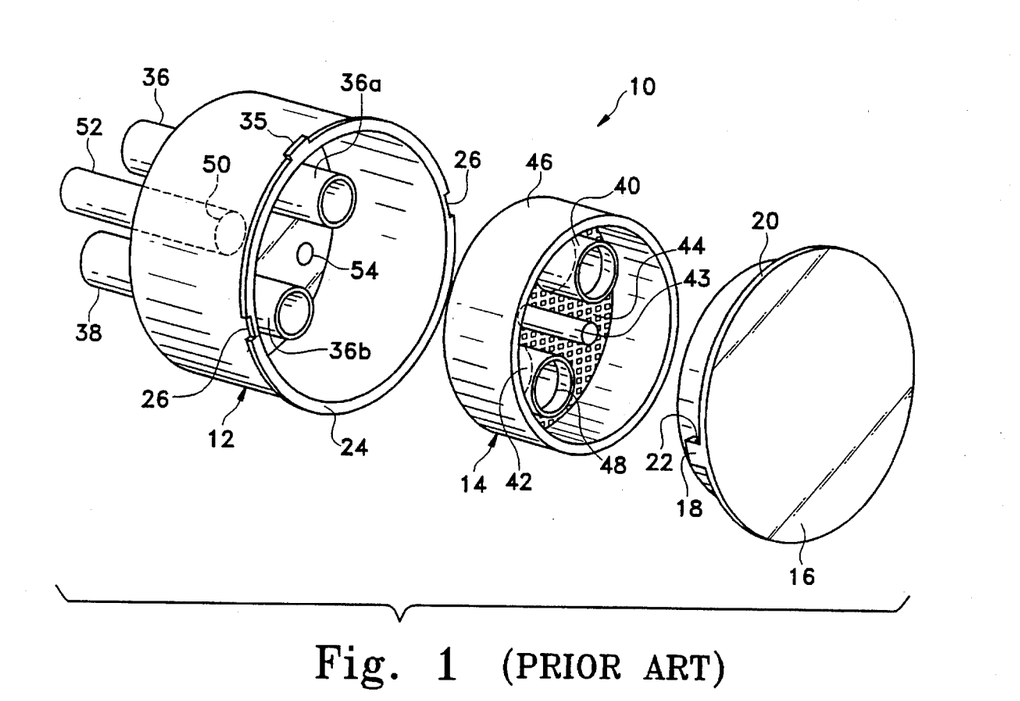
FIG. 1 is an exploded perspective view showing a dental cuspidor filter assembly in accordance with the prior art rotated 90° from its vertical orientation, including a canister, a filter basket and a covering lid rotated 90° from its vertical orientation.

In the drawings, FIG. 1 shows a dental cuspidor effluent filter assembly 10 in a configuration which is typical of the prior art rotated 90° from its vertical orientation. The filter assembly 10 includes a molded plastic canister 12 (e.g. of rigid molded plastic or metal), a replaceable filter basket 14 (which may be of polyethylene, for example) and a covering lid 16. As can be seen from the exploded view of FIG. 1, the lid of the prior art filter assembly is retained to the canister by a pair of depending tabs 18 extending down from a lip 20 of the lid, each tab being generally hook shaped, with an inwardly extending nipple 22. This pair of tabs 18 requires the lid to be oriented at a prescribed rotational position to enable securing of the lid down onto to a top lip 24 of the canister. At that point, the nipples 22 have passed through notches 26 in the upper lip and are below the level of the upper lip of the canister. Thus, the lid can be rotated to a locking position wherein the tab nipples 22 are tightly retained under the upper lip 24 of the canister. The canister covering lid typically includes an O-ring (not shown) in a recess in the underside of the closure lid. The O-ring is tightly engaged against the surface of the upper lip 24 when the lid has been installed and rotated to the locked position. The locked position may be defined by one or a pair of stops 35 on the periphery of the canister, as shown.

As also shown in the prior art drawing of FIG. 1, the canister 12 has a series of openings at its bottom side, comprising inlets and outlets for the filter assembly. A pair of integrally molded depending tubes 36 and 38 preferably are provided, for parallel inflow of fluids from the cuspidor to be filtered. At the interior of the canister these tubes continue, extending upwardly as collar extensions 36a and 36b as shown, so that the filtered material is received into the canister at an elevated position. As seen in the drawing, the filter basket 14 has a pair of similar but larger-diameter tubes or collars 40 and 42, which slide down over the interior canister uprights or collars 36a and 36b.

A lifting stem or post 43 extends up from the bottom of the filter basket to enable removal of the basket.

The filter basket has a perforated bottom 44 for the filtration function, with a peripheral annular wall 46 extending up from the periphery of the bottom. The tubular uprights or collars 40 and 42 in the filter basket have stops 48 comprising an internal diameter reduction, for the purpose of holding the filter basket at a somewhat elevated position above the bottom of the canister. Thus, the filtrate from the filter basket has a plenum below the basket in which to collect. The filtrate exits the filter canister through an outlet opening 50, again with a tubular collar 52 for connection of a transfer conduit tube (not shown) which is a high volume suction line. This aids in the filtration function by applying a negative pressure below the filter basket. An additional opening 54 and tube connection collar (not shown) depending from the bottom of the canister may be provided for various types of cuspidor systems well known in the dental field.

Figure 2:
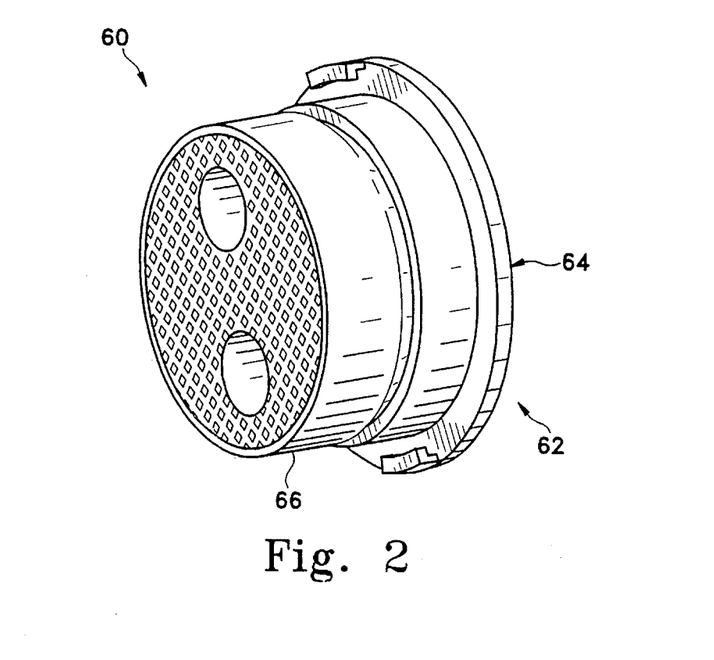
FIG. 2 is a perspective view showing a dental cuspidor filter basket/lid assembly according to the present invention.

FIG. 2 shows a dental cuspidor filter/lid assembly 60 of the present invention rotated 90° from its vertical orientation. The canister which receives the filter basket/lid 60 preferably is identical to the conventional canister described above and shown in FIG. 1, so that the invention can be used directly with the existing dental filter assembly in the dentist's office.

Figure 3:
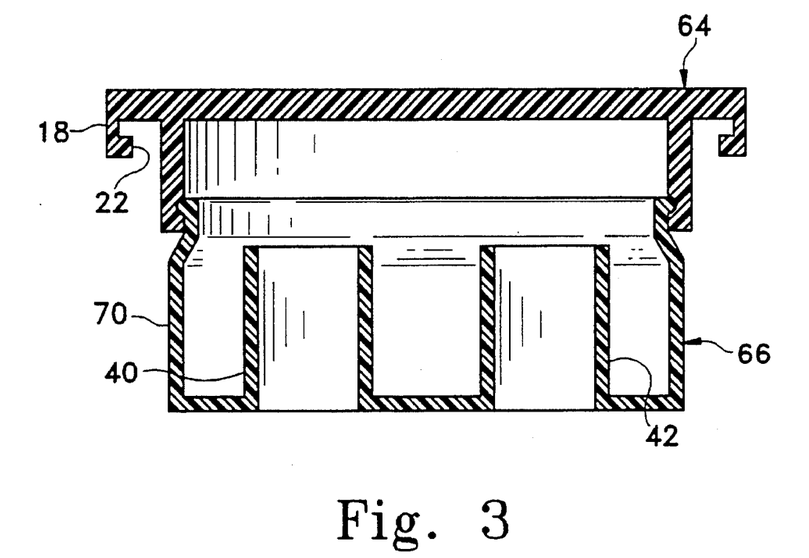
FIG. 3 is a more detailed view showing the combination lid and filter basket of the invention.
Figure 4:
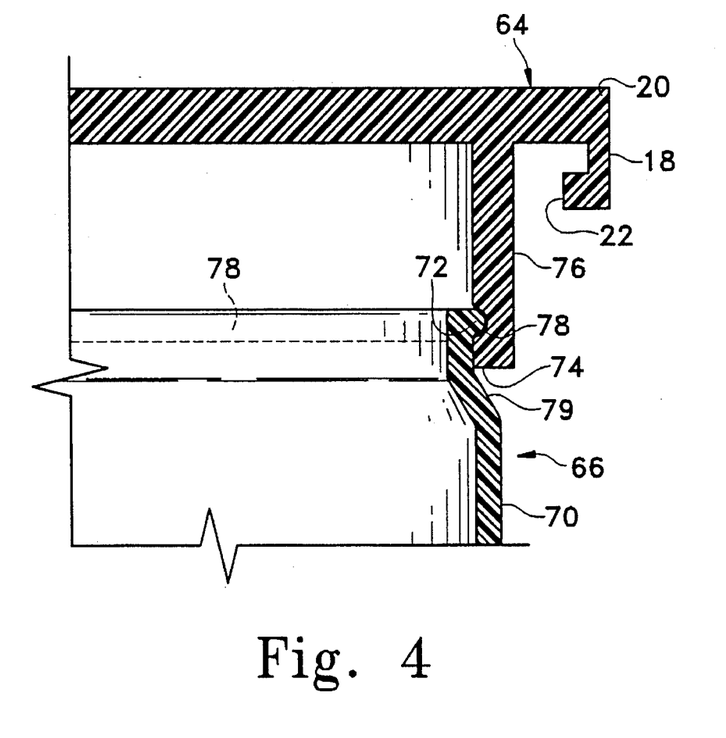
FIG. 4 is an enlarged detail sectional elevation view showing a part of the filter basket and lid assembly and indicating one connection arrangement which can be employed to hold the filter basket and lid together.

In one specific embodiment the combined closure lid/filter basket 60 is formed of two assembled components 64 and 66, snapped together as shown in FIGS. 3 and 4. Both of these components are preferably designed to be disposable, so that when the lid or closure is removed from the canister 12, the entire assembly 62 is discarded and another is put in its place. The drawings show one specific embodiment of a configuration for securing the filter basket 66 to the covering lid 64, and it should be understood that several other configurations are possible within the principles of the invention. In the arrangement shown, the filter basket 66 has an annular outer peripheral wall 70 which is generally the same as that of the conventional configuration described above, but with an outwardly extending lip 72 which will snap together with the covering lid by being forced within the slightly smaller-diameter annulus of an inwardly extending bump or lip 74 on a downwardly extending cylindrical collar 76 of the lid component, and preferably into an annular groove 78. This is best seen in the enlarged detail sectional view of FIG. 4. The wall 70 may angle inwardly as shown at 79 so that the components fit the conventional canister's interior. This configuration is one which allows the covering lid 64 to engage with the canister 12, i.e. a conventional canister, in precisely the same way as the conventional lid for the canister as described above. Depending tabs 18 and locking nipples 22 as in the conventional lid are shown in FIGS. 3 and 4. The snap together connection also permits relative rotation of the lid and basket, permitting rotational locking of the lid as described above.

The closure or covering lid 64 may be formed of clear polypropylene, low-density polyethylene or similar plastic material which may be semi-rigid or flexible.

As shown in the drawing figures, the lifting stem 43 of the conventional filter basket described above (and shown in FIG. 1) is eliminated in the combined lid/filter basket assembly 62 of the invention.

Figure 5:
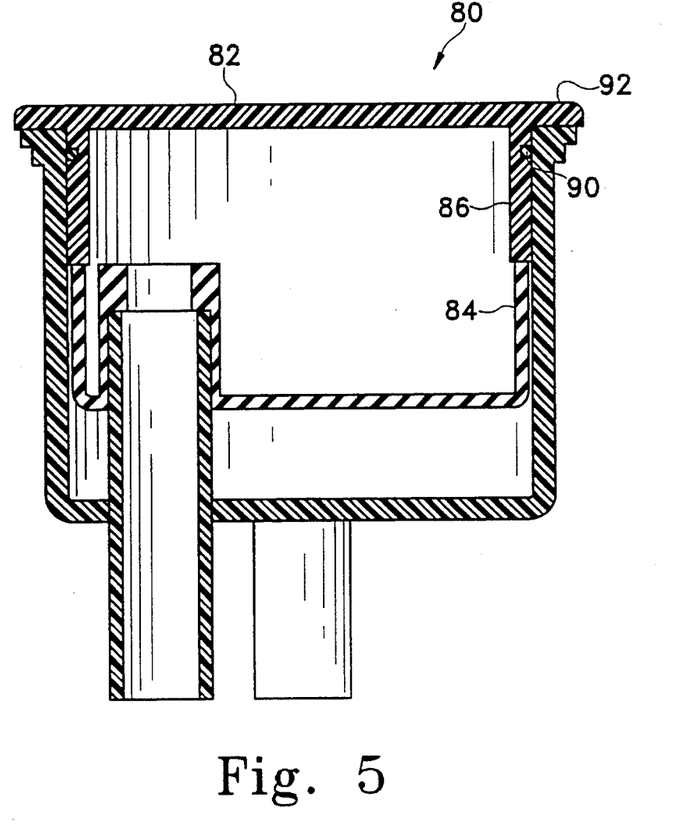
FIG. 5 is a sectional view showing another embodiment of a lid/filter basket assembly, with another connection arrangement.

FIG. 5 shows an alternative embodiment 80 of the closure lid/filter basket assembly of the invention, as seated in a conventional filter canister 12. In this embodiment the lid 82 is of a somewhat different configuration. The filter basket 84 is fixed to a downwardly extending annular flange 86 of the lid, not necessarily allowing for rotation between the two. The filter basket may be connected to the lid by, for example, heat sealing, sonic bonding, adhesive or solvent bonding or other appropriate securing means. If relative rotation of the lid and the basket is not permitted by the connection, the basket must be located at the proper rotational orientation in order to line up the tube collars for the inlets in the canister, in the same arrangement as described above. The canister 12 remains the same as described. Thus, the lid 82 of this embodiment simply seats into the rim of the canister, without the rotational locking device described previously. An O-ring 90 preferably is provided seated in the outside of the depending flange 86, to form a tight fit with the interior rim of the canister when the lid is pressed in. In the engaged position of the lid, the outer rim 92 of the lid simply rests against the top lip of the canister, as shown. In this embodiment the relatively tight engagement of the O-ring seal with the interior of the canister, in combination with the vacuum which is applied to the filtration from below the filter basket, is relied on to retain the lid in place during use.

When a new lid/filter basket assembly is to be placed on the filter canister, the assembly 80 is simply lowered part way into the canister and rotated until the inlet tubes and collars line up, allowing the lid/filter basket assembly 80 to be pushed the remaining distance into place.

The described embodiments of filter basket/lid assemblies can each be efficiently produced as two separately molded components, later assembled together as by snap fitting them together or bonding them, as shown and described. It is also contemplated that the lid/filter basket can be molded as one single component, using a sophisticated form of rotocasting, such an integrally molded article being similar to what is shown in FIG. 5. This is particularly true if the upwardly extending collars 40 and 42 of the filter basket, shown in FIG. 1 and also in FIG. 5, are eliminated. An accurately formed hole at the bottom of the filter basket, at each location, can eliminate the need for the upwardly extending collars, provided these holes either are sized to be press fit down onto the inlet collars 36a and 36b (FIG. 1) of the canister, or the tolerance is made close enough not to pass any filtrate larger than that which the filter mesh 44 is designed to pass. In a rotocast combination unit, the filter mesh openings can be punched after the initial rotocasting of the device. The rotocast version is similar to the embodiment shown in FIG. 5, with the depending flange or lip 86 of the lid simply continuing down to form the generally cylindrical filter basket. A seat or groove can be included in the outside of this lip or flange to seat the O-ring 90 for sealing, as in FIG. 5. The seal is not necessary for contamination considerations, but is helpful in making the vacuum applied to the filter basket more effective. The vacuum actually holds the lid down on the canister but without a seal it can leak and sometimes cause a whistling sound.

For the rotocast embodiment, preferably a soft plastic is used, such as polycarbonate, acrylic or nylon, or other plastics adaptable to rotocasting.

Figure 6:
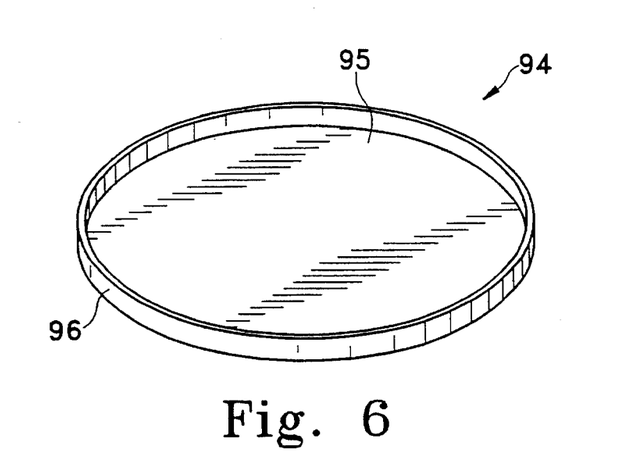
FIG. 6 is a perspective view showing a bottom closure which may be provided to snap over and close the bottom of the disposable filter basket.

FIG. 6 shows a bottom cap or cover 94, formed preferably of a flexible plastic material such as polyethylene or polypropylene and having a bottom surface 95 and an annular lip 96. The internal diameter of the lip 96 is sized to snap over the bottom of the filter basket, such as the filter basket 84 of FIG. 5 or the basket 66 of FIG. 3 or FIG. 2. A friction fit, requiring a slight deformation of the inner lip 96, assures that such a plastic bottom closure will be securely retained on the bottom of the filter basket to effectively close the entire filter basket. Such enclosure of filtered materials inside the basket may be required at some point in dental offices.

Figure 7:
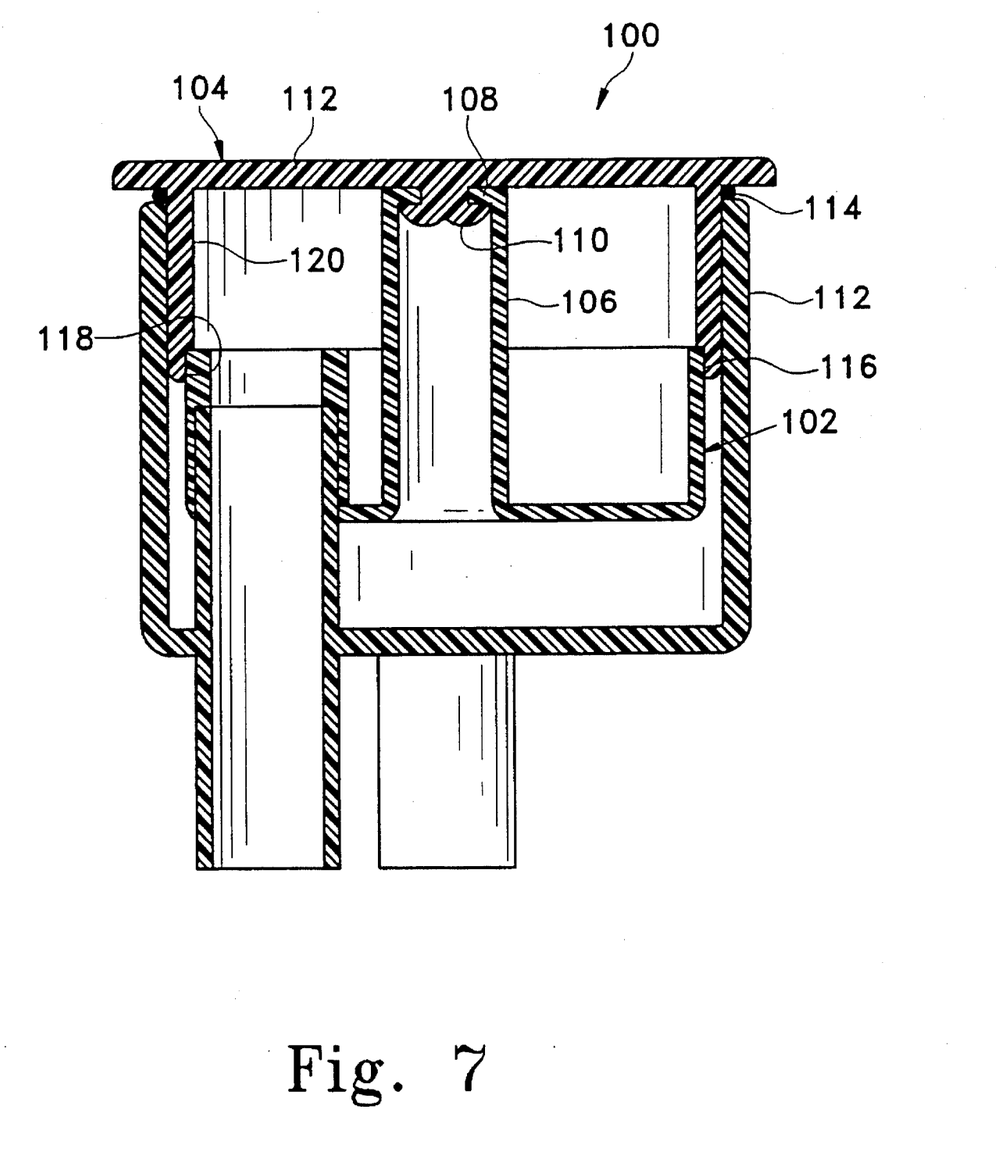
FIG. 7 is an elevational section view showing another embodiment of a lid/filter basket assembly, as two components secured together by a further form of connection.

FIG. 7 shows a further embodiment of a two-component lid/filter basket assembly 100, as contained within a standard filter canister 12, similar to that described above. In this form of the invention a filter basket 102 is secured to a lid or cover 104 by a central tubular stem 106 having a top opening with a lip 108 as illustrated. The lip 108 around the opening forms a snap-in connection for a barb-shaped projection 110 extending down from the generally planar, circular top disk 112 of the lid. The lid may fit into the canister 12 and lock down to the canister in the same manner as in a conventional lid such as shown and described relative to FIG. 1, although it can simply fit closely into the canister as illustrated, with an O-ring 114 included on an outer portion of the lid as indicated. The purpose of the O-ring seal is as described above.

As can be envisioned from FIG. 7, a filter basket 102 is to be fitted onto the lid, simply by lining it up centrally and pushing it into the lid, whereby the opening and lip 108 in the tubular stem 106 of the basket, being of somewhat flexible plastic, yields somewhat to snap over the tapered, barb-like projection 110 at the center of the lid. The annular lip 108 clears the barb 110 and snaps into place. At the same time, the filter basket has an outer peripheral edge 116 which seats within a recess 118 formed in the appropriate diameter of the depending annular flange 120 of the lid 104.

Other forms of connections for a two-component lid/filter basket assembly can also be employed. In another preferred embodiment, the assembly is configured so as to have a reusable id but a disposable basket, yet with the two still connected in accordance with the principles of the invention. As illustrated in the further embodiment of FIG. 8, the disposable filter basket again snaps onto the lid, but a mechanism is provided for manually ejecting the filter basket off the lid when the filter is to be changed, without the hygienist or technician having to touch the used filter basket.

Figure 8:
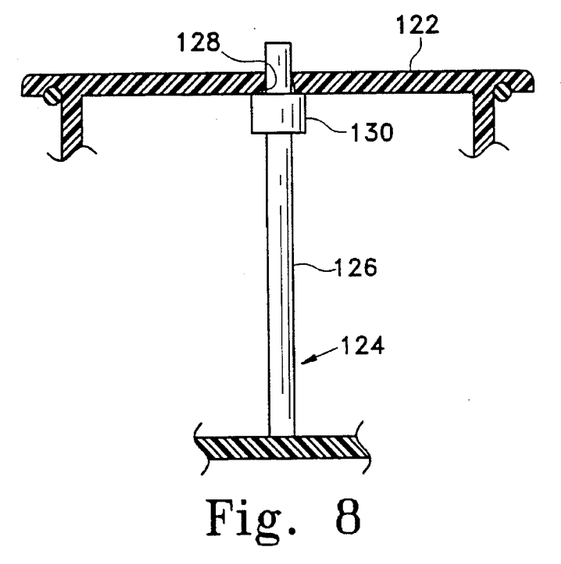
FIG. 8 is an elevational section view similar to FIG. 7, but showing another form of connection between a filter basket and a lid or cover, providing a top-activated release function.

One example of such a manual ejecting mechanism is shown in FIG. 8. FIG. 8 shows fractional portions of a lid or cover 122 (which can be similar to the cover of FIG. 7, for example) and of a filter basket 124, whose central stem 126 is shown, similar to the stem 43 shown in a typical prior art filter basket in FIG. 1. In this case the central stem 126 is made somewhat longer, e.g. about one-half inch to one inch longer than typical in prior filter baskets. The stem 126 fits up into a central opening 128 of the cover 122, in a tight friction fit. The central opening 128 of the cover may be tapered, narrower at top, for the purpose of tightly engaging with the stem 126. If desired the stem can be formed with a shoulder 130 for the purpose of limiting the distance to which the stem 126 is pressed up through the opening 128. When the filter basket 124 is to be changed, the dental technician removes the basket/cover assembly by grasping the cover 122, removes it from the canister and presses down on the top of the stem 126 with the thumb or finger, thereby pushing the stem out of the cover's central opening and releasing the filter basket from the cover.

Figure 9:
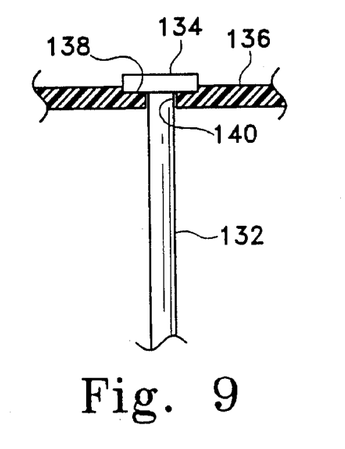
FIG. 9 is a detail view showing an alternative form of connection for the type of device shown in FIG. 8.

FIG. 9 shows a variation of the arrangement shown in FIG. 8. In this case the filter basket stem 132 has a cross bar 134 at its upper end. The cover 136 has an elongated recess 138 into which the cross bar 134 can seat when properly oriented rotationally. The opening 140 in the cover is elongated in shape, so that the cover is inserted over the cross bar 134 in proper orientation, then the two components are adjusted 90° relative to one another so that the cross bar seats in the recess 138. This holds the filter basket and cover together while allowing the dental practitioner a simple means of releasing the filter basket for disposal, without touching the filter basket itself. The over 136 is simply re-rotated 90° to the point where the cross bar 134 will fall through the opening 140.

Figure 10:
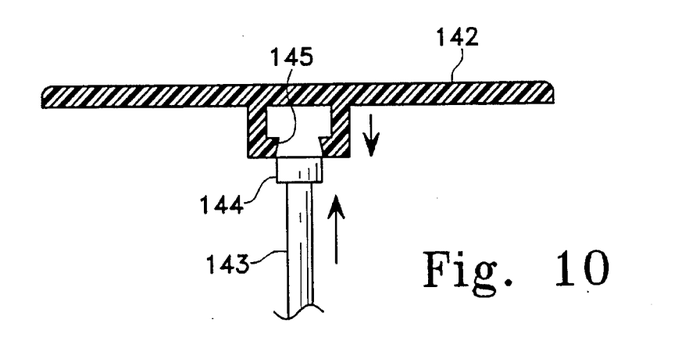
FIG. 10 is a schematic view showing a lid or cover and a stem of a filter basket in a type of assembly which snaps together and permits release from the top side.
Figure 11:
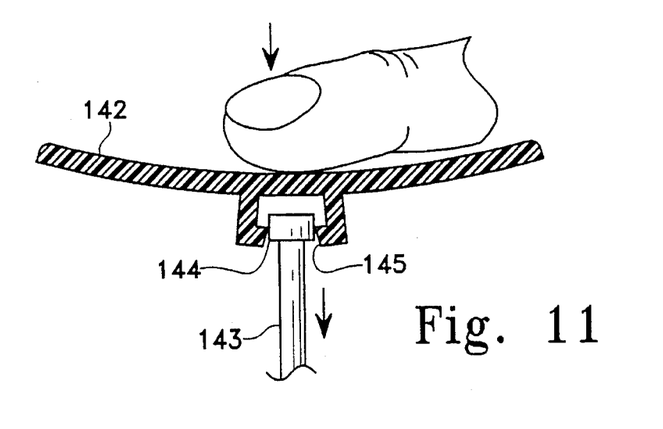
FIG. 11 is a view similar to FIG. 10, illustrating the release of the filter basket stem from the cover or lid.

FIGS. 10 and 11 show another form of filter baskets/cover connection which is readily releasable without the need for the practitioner to contact the dirty filter basket. FIG. 10 schematically indicates a lid or cover 142 and shows a stem 143 of a filter basket being inserted. It should be understood that the cover 142 is shown in simple, schematic form, but it can comprise any of the covers described herein which are initially formed as separate components from the filter basket. The filter basket stem 143 has a larger diameter head or tip 144 which is sized to snap into a clearance formed by discrete, separate barb elements 145 (such as three or four arranged in a circular pattern). As the lid 142 is pressed down, the head 144 of the basket stem spreads the barb elements 145 apart so that the head 144 snaps into place and the filter basket is captured to the cover.

FIG. 11 shows the release of the filter basket stem 143 from the cover 142. The practitioner simply holds the cover in one hand, between the thumb and forefinger, and presses down on the center of the cover to deflect the center downwardly into a dished shape as shown. The cover may be made of relatively soft plastic material such as polyethylene or polypropylene for this purpose, or it is of sufficiently thin material that it can be deflected in this way. The discrete barb elements 145 spread apart sufficiently due to this deflection of the cover to release the head 144 of the filter basket, so that the filter basket drops into a waste disposal area as desired.

Figure 12:
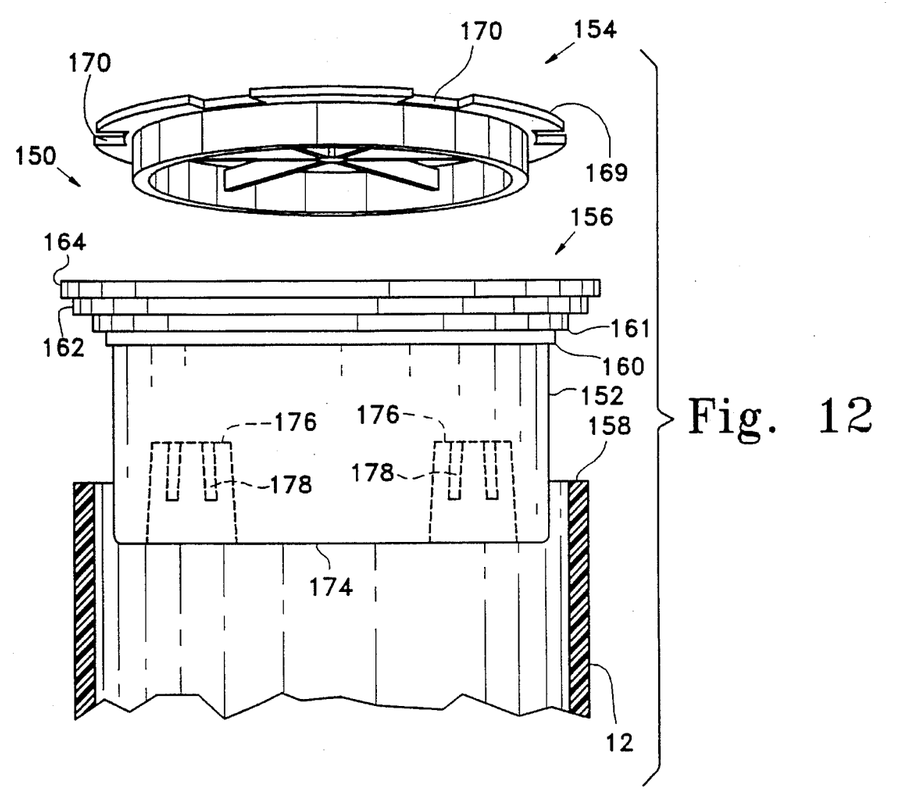
FIGS. 12 and 13 show a further embodiment of the invention, wherein a filter basket rests directly on the filter canister.

FIG. 12 shows another form of filter basket assembly 150, including a filter basket 152 and a filter basket cover 154. In this embodiment the filter basket itself includes an annular lip or flange generally identified as 156, which is of an appropriate diameter to rest on the top edge 158 of the filter canister container. FIG. 12 illustrates the annular lip 156 at the top of the filter basket preferably being stepped as shown, with a series of external diameters 160, 161 and 162 for engaging the interior of a canister container such as the container 12 indicated in FIG. 12, and this provides versatility for seating on several different sizes of canister. The final, outer diameter 164 of the lip 156 will be larger than the internal diameter at the top of the canister within which the basket is to be seated.

The lip 156 rests on the top edge 158 of the canister and forms a rough or approximate seal with that edge. As discussed above, vacuum is pulled in the interior of the canister container during operation of the filter, and this is in part relied upon to keep the filter basket and lip 156 firmly seated on the top edge of the canister. Also as above, an O-ring may be provided, or a plurality of O-rings, with one appropriate for the particular dental filter canister with which the assembly is to be used. In some cases one of the external lip diameters will snap in due to flexibility of material.

Figure 13:
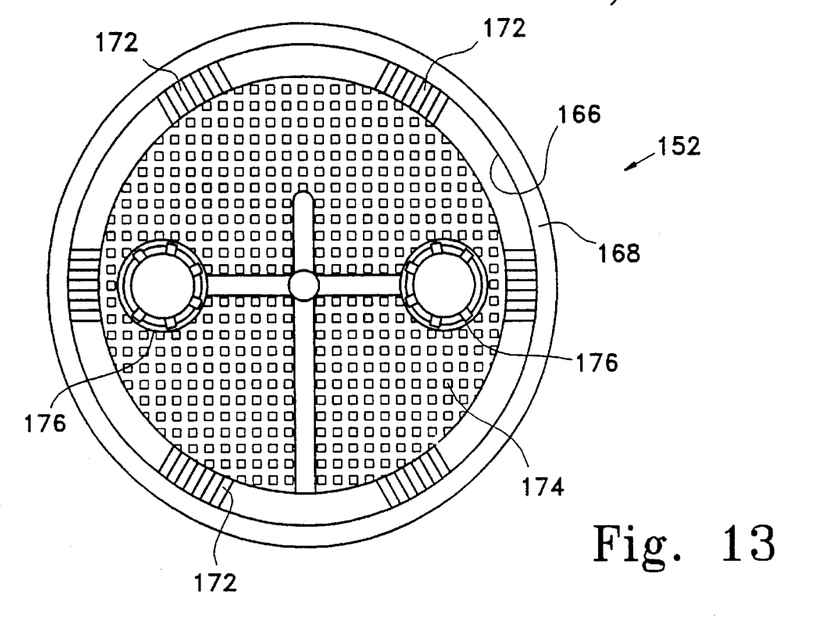

As shown in FIGS. 12 and 13, the filter basket 152 has an annular recess 166 in the lip or flange 156, positioned generally as a flat annular ledge which is just inward of an upwardly extending rim 168. The ledge 166 provides a surface on which a series of tabs 169 of the filter basket cover 154 will rest. The tabs 169 could extend continuously as one single flange around the annulus of the cover 154 if desired, but in this preferred embodiment they are interrupted by notches 170, thus forming discrete tabs 169 as outer extremities of the cover. FIG. 13 shows a series of bosses 172 over which these notches are positioned, to help snap the cover into place on the filter basket. These bosses and notches can be helpful in a form of the device wherein the cover 154 is permanently secured to the filter basket 156 by ultrasonic bonding. Such permanent bonding of the cover with the basket prevents any reuse of the filter basket, which is desirable from the standpoint of avoiding contamination.

The basket 152 has a perforated bottom 174 which may be generally flat as shown in FIGS. 12 and 13. The perforated bottom may be molded as a matrix of perpendicular bars or lines, forming generally square holes between them (detail not shown), or it may be formed with round holes. As shown in the drawings, a pair of upright tubular collars 176 are integrally formed with the bottom 174 and extend upwardly therefrom. These tubular collars are designed and positioned so as to make the filter basket 152 fit several different sizes and arrangements of dental filter canisters, cooperating with the plurality of ledge diameters 160, 161, 162 on the lip 156 of the filter basket. The upwardly extending collars each are tapered inwardly toward their upper ends, to fit closely over canister inlet tubes of slightly differing outside diameters. Also, these collars may be flexible and oversized at their bottom openings to accommodate inlet tubes of slightly differing spacings from canister type to canister type. So that they will still engage the outside of the inlet tubes, the upright collars 176 have vertically arranged slits 178 arranged around their circumference with, for example, six of these slits 178 provided. This in combination with the tapered shape of each collar helps engage with different inlet tube diameters and spacings for different dental filter canister assemblies.

The above described preferred embodiments are intended to illustrate the principles of the invention but without limiting its scope. Other embodiments and variations to these preferred embodiments will be apparent to those skilled in the art and may be made without departing from the essence and scope of the invention as defined in the claims. Specifically, the orientation of the system can be slightly rotated from its vertical orientation without interfering with the parameters of normal operation.

I claim:

1. A filter canister assembly for receiving waste from a dental cuspidor, comprising:

a canister generally defining an internal chamber and having an open end, an outlet means, connected to the canister and in fluid communication with the internal chamber, for connection to a source of suction to be applied to the canister, inlet means in fluid communication with the interior of the chamber of the canister, for delivering waste material from said cuspidor, to be filtered, and a disposable canister closure fitted to said open end of the canister, the closure having means for engagement with the canister to close the open end and for generally providing a seal with the canister when engaged with said open end, with a disposable filter secured to an underside of the canister closure by securing means, the disposable filter being so positioned in the internal chamber of the canister, when the closure is engaged on the canister, as to receive suction from the outlet means against an outlet side of the filter and to receive waste material from the inlet means at an opposite, inlet side of the filter, whereby the filter of the filter canister can be quickly changed by removal and disposal of the canister closure and attached filter and replacement with another disposable canister closure/filter combination.

2. The filter canister assembly of claim 1, wherein the securing means comprises a snap fit means for engaging the canister closure with the disposable filter when the filter is pushed tightly into engagement with the canister closure.

3. The filter canister assembly of claim 2, wherein the snap fit means comprises a central tubular stem on the disposable filter, extending sufficiently to reach a bottom surface of the canister closure, a rimmed opening at a end of the tubular stem, and a barb-shaped projection extending from said bottom surface of the canister closure, sized and configured to snap within the rimmed opening of the tubular stem when the filter is pushed tightly against the canister closure.

4. The filter canister assembly of claim 2, wherein the disposable filter comprises a filter basket and the snap fit means comprises central stem on the disposable filter, extending sufficiently to reach a surface of the canister closure, and means cooperative between a end of the central stem and said surface of the canister closure for snapping together the canister closure and the central stem when the filter basket and canister closure are pushed together.

5. The filter canister assembly of claim 1, wherein the canister closure includes a generally annular flange and wherein the disposable filter comprises a filter basket having an annular wall, and wherein the securing means comprises means for latching together a rim of the filter basket's annular outer wall with a end of the flange of the canister closure.

6. The filter canister assembly of claim 1, wherein the disposable canister closure and the disposable filter are permanently secured together with said securing means.

7. The filter canister assembly of claim 1, wherein the disposable filter comprises a filter basket sized to fit within the internal chamber of the canister, the filter canister assembly further including a cover means, separate from the canister, closure and filter, for fitting securely over said filter basket after the closure and filter have been removed from the canister, to close and seal off the interior of the filter basket whereby waste material within the filter basket can be contained for storage within a waste container.

8. A filter canister assembly for receiving waste from a dental cuspidor dental suction system and saliva ejector system, comprising:

a canister generally defining an internal chamber and having an open end, an outlet means connected to the canister and in fluid communication with the internal chamber, for connection to a source of suction to be applied to the filter canister, inlet means in fluid communication with the interior of the internal chamber of the canister, for delivering waste material from said cuspidor to be filtered, a canister closure fitted to said open end of the canister, a disposable filter with securing means for connecting the disposable filter to the closure, and the disposable filter being positioned in the internal chamber so as to receive suction from the outlet means against an outlet side of the filter and to receive waste material from the inlet means at an opposite inlet side of the filter, the connected canister closure and disposable filter having means for engaging against the canister so as to close the open end of the canister, and filter release means for releasing said securing means to disengage the disposable filter from the canister closure when the release means is engaged by an operator holding the canister closure, without requiring contact by the operator with the disposable filter, whereby the filter of the filter canister can be quickly changed by the operator by removal of the canister closure and attached filter, release of the disposable filter from the canister closure without contact of the operator with the filter, and replacement with another disposable filter, connected to the canister closure by said securing means.

9. The filter canister assembly of claim 8, wherein the disposable filter has a central stem and having an end, and snap-together means cooperative between said end of the stem and a surface of the canister closure for engaging the closure with the stem by pushing the filter and closure together.

10. The filter canister assembly of claim 9, wherein the filter release means comprises means for pressing on the center of said canister closure while holding the outer periphery of the canister closure, with the closure and filter removed from the canister, to release the securing means.

11. The filter canister assembly of claim 9, wherein the securing means comprises an opening in the canister closure positioned to receive said end of the stem from the filter in a friction fit engagement such that the stem extends through the opening, whereby the operator can push on said end of the stem to release the stem from the opening, thus disengaging the disposable filter from the canister closure.

12. A filter canister assembly for receiving waste from a dental cuspidor, comprising:

a canister generally defining an internal chamber and having an open end, an outlet means connected to the canister and in fluid communication with the internal chamber for connection to a source of suction to be applied to the filter canister, inlet means in fluid communication with the interior of the internal chamber of the canister and said cuspidor, for delivering waste material from said cuspidor, to be filtered, and a disposable filter basket fitted into said open end of the canister, having a generally cylindrical wall and a perforated end, positioned within the canister so as to receive suction from the outlet means against an outlet side of the filter and to receive waste material from the inlet means at an opposite inlet side of the filter, the filter basket including an annular lip at the cylindrical wall and the lip having a diameter sufficient to rest on an edge of the canister when the filter basket is positioned in the canister, so as to close said open end and generally seal the filter basket against the upper edge of the canister, and a closure seated at the cylindrical wall of the filter basket, closing the open end of the filter basket.

13. The filter canister assembly of claim 12, including means for snapping the closure onto the filter basket.

14. The filter canister assembly of claim 12, wherein the closure is permanently secured to the filter basket.

15. The filter canister assembly of claim 12, wherein the annular lip of the filter basket includes an annular recess, and the closure being sized to fit closely within the annular recess so as to snap into place.

16. The filter canister assembly of claim 12, wherein the inlet means of the canister includes a generally cylindrical tube extending into the canister of the canister, and wherein the filter basket includes, extending from the perforated end, a tubular flange having slits extending from an end so as to accommodate and grip onto different outside diameters of tubes for delivering waster material from the cuspidor.

17. The filter canister assembly of claim 16, wherein the inlet means includes two cylindrical tubes extending in the canister, and wherein two openings and tapered tubular flanges are included on the filter basket, positioned to fit over the two cylindrical inlet tubes.

18. The filter canister assembly of claim 12, wherein the annular lip of the filter basket comprises a series of stepped lip segments of diameters which increase in stepped fashion from a innermost annular lip segment to an outermost annular lip segment, whereby the filter basket's annular lip will fit several different diameters of filter canisters each having a rim, with one of the annular lip segments engaging against said rim of a canister in each case.

19. The filter canister assembly of claim 12, further including a cover means, separate from the canister, closure and filter, for fitting securely over said perforated end of the filter basket after the closure and filter have been removed from the canister, to close and seal off the interior of the filter basket whereby waste material within the filter basket can be contained for storage within a waste container.

20. A filter canister assembly for receiving waste from a dental cuspidor, comprising:

a filter canister generally defining an internal chamber and having an open end, an outlet means connected to the canister and in fluid communication with the internal chamber for connection to a source of suction to be applied to the filter canister, inlet means in fluid communication with the interior of the internal chamber of the filter canister, for delivering waste material from said cuspidor to be filtered, a closure fitted to said open end of the canister, a disposable filter comprising a filter basket with securing means for connecting the disposable filter to the closure, and the disposable filter being positioned in the internal chamber so as to receive suction from the outlet means against an outlet side of the filter and to receive waste material from the inlet means at an opposite inlet side of the filter, the connected closure and disposable filter having means for engaging against the canister so as to close the open end of the canister, filter release means for releasing said securing means to disengage the disposable filter and from the canister closure when the release means is engaged by an operator holding the canister closure, without requiring contact by the operator with the disposable filter, whereby the filter of the filter canister can be quickly changed by an operator by removal of the closure and attached filter as a single unit, without contact of the operator with portions of the filter which have extended into the canister.

21. The filter canister assembly of claim 20, further including a cover means, separate from the canister, closure and filter, for fitting securely over the filter basket after the closure and filter have been removed from the canister, to close and seal off the interior of the filter basket whereby waste material within the filter basket can be contained for storage within a waste container.

* * * * *